(12) United States Patent
Pallado et al.

(10) Patent No.: US 6,214,384 B1
(45) Date of Patent: Apr. 10, 2001

(54) NANOSHERES COMPRISING A BIOCOMPATIBLE POLYSACCHARIDE

(75) Inventors: Paolo Pallado, Padova; Luca Benedetti; Lanfranco Callegaro, both of Vicenza, all of (IT)

(73) Assignee: Fidia Advanced Biopolymers S.r.l., Brindisi (IT)

( * ) Notice: Subject to any disclaimer, the term of this patent is extended or adjusted under 35 U.S.C. 154(b) by 0 days.

(21) Appl. No.: 08/938,288

(22) Filed: Sep. 26, 1997

(51) Int. Cl.[7] .............................. A61K 9/19; A61K 48/00; A61K 51/00
(52) U.S. Cl. ...................... 424/493; 424/9.322; 424/489; 424/434; 424/405; 504/116
(58) Field of Search ........................................ 424/489, 464, 424/449, 448, 493, 9.322, 405, 434; 504/116

(56) References Cited

U.S. PATENT DOCUMENTS 5,565,188 * 10/1996 Wong et al. ..................... 424/9.411
5,594,091 * 1/1997 Igari et al. ............................ 528/271
5,607,691 * 3/1997 Hale et al. ............................ 424/449

* cited by examiner

*Primary Examiner*—Thurman K. Page
*Assistant Examiner*—William E. Benston, Jr.
(74) *Attorney, Agent, or Firm*—Hedman, Gibson & Costigan, P.C.

(57) ABSTRACT

Microspheres, having a size lower than $1\mu$ and comprising a biocompatible polysaccharidic polymer, are prepared with a process comprising the precipitation of polymer induced by means of a supercritical antisolvent (SAS). These microspheres are used as vehicling agents or carriers in the preparation of pharmaceutical compositions administrable by oral, nasal, pulmonary, vaginal or rectal route. These microspheres can also be advantageously used as vehicling agent or carriers in the preparation of pharmaceutical compositions for the treatment of human diseases associated with genic defects, for the preparation of diagnostics and in the agro-alimentary industry.

14 Claims, 3 Drawing Sheets

NANOSPHERES COMPRISING A BIOCOMPATIBLE POLYSACCHARIDE

FIELD OF THE INVENTION

The present invention relates to: microspheres having a mean diameter ≧0.1 and <1 μ, comprising a biocompatible polysaccharide polymer and optionally at least one active ingredient, pharmaceutical compositions containing said microspheres administrable by oral, nasal, pulmonary, vaginal or rectal route, the use of microspheres having a mean diameter ranging from 0.1 to 1 μ as carriers for the preparation of pharmaceutical compositions for human genic therapy, for the preparation of diagnostics and in the agroalimentary industry, a process for the preparation of microspheres having a mean dimension of between 0,1 and 1 μ comprising the precipitation of said polymer induced by means of a supercritical antisolvent (SAS).

TECHNOLOGICAL BACKGROUND

Major advances have recently been made in pharmaceutical technology to research new methods for the preservation of the intrinsic activity of polypeptides and to render them absorbent. Formulations able to ensure a reproducible absorption of these active molecules have the advantage of lacking side effects, unlike synthetic polymers. Of all the most widely used natural polymers, the category of acidic polysaccharides is of particular interest. One of these, hyaluronic acid, a polysaccharide widely distributed throughout animal organisms, is constituted by units of D-glucuronic acid and N-acetyl D-glucosamine in alternate order. Its molecular weight can vary according to the methods used for its extraction and/or purification (EP 0138572 reg. on 25.7.90; EPA 0535200 published on 7.4.93; PCT Application No. WO 95/04132 published on 9.2.95; PCT Patent Application No. WO 95/24497 published on 14.9.95).

Besides the polymer's chemical-physical properties, the release methods and systems for biologically active molecules are also particularly important, such as microspheres which seem to be among the most versatile release systems. EPA 0517565 discloses a process for the preparation of microspheres, whose dimensions range between 1–100 μm, wherein the polysaccharide ester dissolved in an aprotic solvent such as DMSO, is added to a mixture of a high-viscosity mineral oil containing a non ionic surface active agent and ethyl acetate, which is a solvent for DMSO and the mineral oil, but not for the polysaccharide ester, which therefore precipitates in the form of microspheres having therefore the above mentioned dimensions.

Today, various techniques are known which involve the use of supercritical fluids for the production of finely subdivided particles with a narrow granulometric distribution curve. The supercritical antisolvent process is generally performed at moderate temperatures and enables the solvent to be completely removed from the precipitation environment. The applications concern substances that are heat-sensitive or difficult to handle, such as explosives (Gallagher, P. M. et al.. 1989, *Supercritical Fluid Science and Technology*—Am. Chem. Soc. 334–354). Other applications concern the production of polymers in the form of fibers (Dixon, D. J. et al, 1993, *J. Appl. Polym. Sci.* 50, 1929–1942) and in the form of microparticles, including microspheres (Dixon, D. J.,et al., 1993, *AIChE J.*, 39, 1, pp 127–139). In the pharmaceutical field, the main interest is in the treatment of proteins (Tom, J. W., et al, 1994, *Supercritical Fluid Engineering Science*, pp 238–257, ACS Symp. Chap. 19, Ed. H. Kiran and J. F. Brennecke; Yeo, S. D., et al, 1993, *Biotech. and Bioeng.*, 41, pp 341–346) and biodegradable polymers, such as poly(L-lactic acid) (Randolph, T. W., et al, 1993, *Biotechnol, Prog.*, 9, 429–435; Yeo, S. D., et al, 1993, *Macromolecules*, 26, 6207–6210). Various methods have been devised for precipitation with a supercritical antisolvent. The semi-discontinuous method (Gallagher et al., 1989), involves injection of the antisolvent in the liquid solution which has already been prepared in the desired working conditions. The operation must be performed in a stepwise fashion to ensure that the liquid is removed, the final quantities of product are very limited and the spheres measure far more than 1 μ in size. Precipitation with a compressed antisolvent (PCA) involves injection of the solution in the high-density supercritical fluid (SCF) (Dixon et al., 1991; Dixon and Johnston, 1993). The injection times are much reduced to guarantee complete dissolution of the liquid, so the quantity of precipitate is very low, giving microfibers with an ordered structure.

The continuous process (Yeo et al., 1993a) enables the solution and the antisolvent to be injected simultaneously in the precipitation environment; the liquid expands and evaporates in the continuous phase, constituted by the SCF. The solution is injected through a micrometric nozzle with a diameter ranging between 10 and 30μ. Solutions must be diluted to avoid blocking the nozzle and to prevent reticulate structures being formed. Consequently, the quantity of solid solute injected is very low. Moreover, a high ratio between the volume of antisolvent and solution must be used to continuously remove the liquid solvent from the precipitation vessel.

When the solution is placed in the precipitator and the container is loaded by means of SCF up to the desired pressure, the process assumes a completely discontinuous character (Yeo et al., 1993 a,b). By this technique, microspheres with a diameter of over 1 μ have been obtained. All the methods described here are accompanied by a final washing step to prevent the precipitate being resolubilized by the solvent. However, none of the cited techniques has been specifically applied to the production of high-molecular-weight biocompatible polysaccharide polymers and in particular the HYAFFs, namely the ester of hyaluronic acid, which are obtained by the procedure described in U.S. Pat. No. 4,851,521.

SUMMARY OF THE INVENTION

The Applicant has unexpectedly found that with the discontinuous SAS technique it is possible to obtain in quantitative yields microspheres with a diameter of less than 1 μ comprising an ester of a biocompatible acidic polysaccharide polymer, selected from the group consisting of: hyaluronic acid esters, crosslinked esters of hyaluronic acid, esters of chitin, esters of pectin, esters of gellan, esters of alginic acid.

Object of the present invention are therefore microspheres having a mean dimension ≧0.1 μ and <1 μ comprising a biocompatible polysaccharide a polymer.

A further object of the present invention are pharmaceutical compositions administrable by oral, nasal, pulmonary, vaginal or rectal route, containing said microspheres as vehicling agents or carriers in combination with at least one active ingredient and optionally with further conventional excipients.

A further object of the present invention relates to said microspheres further comprising at least one of the following active principles: a pharmaceutically active polypeptide, a Granulocyte Macrofage Colony Stimulating Factor (GMCSF), a trophic factor, an immunoglobulin, a natural or a synthetic derivative of a ganglioside, an antiviral, an antiasthmatic an antiinflammatory agent, an antibiotic and an antimycotic agent.

A further object of the present invention relates to pharmaceutical compositions administrable by oral, nasal, pulmonary, vaginal or rectal route containing the microspheres inglobating the above mentioned active principles, optionally in combination with other conventional excipients.

A further object of the present invention relates to the use of said microspheres as carriers in the preparation of diagnostics and in agroalimentary industry. Moreover the microspheres having a diameter ranging from 0.1 to 1 μ containing a biocompatible acidic polysaccharide ester selected from the group consisting of:hyaluronic acid esters, esters of chitin, esters of pectin, esters of gellan, esters of alginic acid can be advantageously used as vehicling agent or carriers of a gene, for the preparation of pharmaceutical compositions for the treatment of diseases associated with genic defects.

A further object of the present invention resides in the discontinuous a process for the preparation of microspheres having a dimension comprised between 0.1 and 1 μ and comprising the precipitation of said polymer induced by means of a supercritical antisolvent (SAS). The process object of the present invention comprises the following steps:

a) dissolving the polysaccharide biocompatible polymer in an aprotic solvent at concentrations ranging from 0.1 to 5% by weight, b) charging the solution of step (a) in a pressure proof container having at the top and at the base steel filters with an average cutoff lower than 0.1 μ;

c) loading from underneath the antisolvent until reaching the pressure at which said fluid becomes supercritical at a temperature ranging from 25 to 60° C., d) removing the aprotic solvent, by flowing said supercritical fluid, e) depressurizing the pressure proof container and collecting the precipitated product.

Contrarily to what one could foresee from the above mentioned prior art (teaching that, with the SAS discontinuous technique, process times are longer than with the continuous one, nucleation occurs in the bulk liquid phase where the supercritical antisolvent is dissolved and therefore the formation of large particles with broad granulometric distribution is expected) surprisingly the expanding conditions adopted with the process according to the present invention enable the onset of the nucleation process in a well-expanded media so that the formation of a high number of nucleation centers is achieved. This factor, combined with the amorphous nature of the solid solute, leads to the formation of microspheres whose dimension is comprised in the above mentioned range and moreover with a narrow granulometric distribution curve.

DETAILED DESCRIPTION OF THE INVENTION

The biocompatible polysacharide polymer which is comprised in the microspheres according to the present invention is preferably an ester of a polysaccharide said such a hyaluronic acid ester, selected from those described U.S. Pat. No. 4,851,521, which we incorporate by reference, a crosslinked ester of hyaluronic acid selected from those disclosed in EP 0341745 B1 which we incorporate by reference, an ester of chitin selected from those described in PCT WO93/06136, which we incorporate by reference, an ester of pectin selected from those mentioned in PCT WO93/14129, which we incorporate by reference, an ester of gellan selected from those disclosed in U.S. Pat. No. 5,332,809, which we incorporate by reference, an ester of alginic acid selected from those reported in U.S. Pat. Nos. 5,264,422 and 5,336,668, which we incorporate by reference. Particularly preferred esters are the total or partial benzyl ester of hyaluronic acid. Among the partial ester a particularly preferred ester is the benzyl ester with 75% of the carboxy function of hyaluronic acid esterified with benzyl alcohol.

The pharmaceutical compositions according to the present invention containing said microspheres as vehicling agents or carriers, in combination with at least one active agent can optionally be formulated in a controlled release form, in order to have the desired rate of absorption, with suitable excipients normally used for preparing this type of formulations.

Preferred pharmaceutically active polypeptides which can be comprised in the microspheres according to the present invention are calcitonin, insulin, preferred trophic factors, which can be incorporated in the microspheres according to the present invention are the Nerve Growth Factor (h-NGF), the Ciliary Neuronotrophic Growth Factor (h-CNTF). The pharmaceutical compositions containing the above microspheres incorporating the above listed active principles, can optionally be formulated in controlled release form, in order to have the desired rate of absorption, with suitable excipients normally used for preparing this type of formulations.

As pointed out above the microspheres having a mean diameter $\geq 0.1$ μ and <1 μ can be advantageously used as vehicling agents in the preparation of diagnostics. In particular, according to the type of technique to be used for diagnostic analysis, such as NMR, ultrasound, X rays, the microspheres can be loaded with paramagnetic agents such as magnetite, or they may be concave in structure, or, alternatively, they may be loaded with nonionic contrast agents, or, lastly, with radioactive isotopes such as $TC^{99m}$.

As a matter of fact vehicling of the contrast agents by means of microspheres limits interaction with the blood, thus reducing the onset of the side effects typically caused by contrast agents.

As previously pointed out, another important sector in which the microspheres having a diameter comprised between 0.1 and 1 $\mu$ according to the present invention can be advantageously used is the preparation of pharmaceutical compositions for the treatment of diseases associated with genic defects.

Much effort is currently being put into scientific research in this field to find remedies for genetic-type malformations or metabolic diseases of a genetic origin. Most of the work being done is aimed at identifying and preparing vehicling systems for healthy genetic material to be administered to patients suffering from such malformations and diseases. One of the possibilities is represented by the encapsulation of healthy genes in microspheres which are able to penetrate more deeply into the tissues and sustain contact with the cell surfaces to be treated for longer periods of time. It follows that the adherence of the microspheres to the cell surfaces enables the release of genetic material transported to the close vicinity of the target cells. In particular, the microspheres having a mean diameter ranging from 0.1 to 1 $\mu$ containing the biocompatible polysaccharide polymer according to the present invention represent an ideal transport system for biological material, and in this particular case for healthy genes, thanks to their very small dimensions and specific mucoadhesiveness. Among the possible applications for said microspheres in the treatment of human diseases associated with genic defects a preferred one is in their use as vehicling agents of single genes which encode specific enzymes, for the treatment of diseases caused by a deficit of the same enzymes. There are in fact numerous diseases which derive from an enzyme deficit or hyperactivity, which is caused by defects occurred in the specific gene encoding this enzyme.

For example diseases of this type are:
phenylketonuria, due to a deficit of phenylalanine hydroxylase,
alkaptonuria, due to a deficit of homogentisic acid oxidase,
albinism due to a deficit of tyrosinase and many other diseases involving amino acid Metabolism;
diseases involving glycogen accumulation, some of which are fatal at birth, due to deficit of enzymes such as glucose-6-phosphatase, brancher or de-brancher enzymes, and α-lysosomal glucosidase enzymes;
carbohydrate metabolism disorders
Wilson's disease, involving a defect in ceruloplasma, the protein which transports copper
porphyria caused by a deficit in porphobilinogen deaminase, uroporphyrinogen oxydase, protoporphyrinogen oxydase coproporphyrinogen oxydase,
gout due to hypoxanthine-guanine-phosphoribosyl transferase deficiency, or hyperactivity of 5-phosphoribosyl-1-pyrophosphate
transferase,
diseases involving lysosomal accumulation such as gangliosidosis, due to β-galactosidase deficiency, leukodystrophy, Niemann-Pick's disease due to sphingomyelinase deficiency, Gaucher's disease due to glucosyl-ceramidase deficiency, Fabry's disease, due to α-galactosidase deficiency, mucopolysaccharidosis etc.,
connective tissue disorders (brittle bone syndrome, Ehlers-Danlos syndrome, Marfan syndrome), Besides their use in enzymatic deficits, the microspheres can be used to vehicle single genes in any pathologies wherein such genes are altered, such as malformative diseases of genetic origin (Down's syndrome, arachnodactyly etc.), hereditary diseases such as:
hemoglobinopathies (sickle-cell anaemia, thalassaemia etc),
cystic fibrosis,
primitive hyperlipoproteinemia and other lipid metabolism disorders, wherein single or multifactorial gene disorders with hereditary transmission and complex modalities of different genes, interact with environmental factors, thus determining hyperlipoproteinemia having a different degree of seriousness in different members of the same family,
cancer wherein it has been ascertained that genetic alterations exist at the level of the differentiation and of the failed control of cellular growth.

Finally as pointed out above, the microspheres having a mean diameter $\geq 0.1$ $\mu$ and $<1$ $\mu$ can be advantageously used in the agro-alimentary sector, for example as a vehicle for plant treatments or for the preservation of additives.

The preferred supercritical fluid used as antisolvent in the process according to the present invention is selected from carbon dioxide ($CO_2$) and hydrofluorocarbons, such as trifluoromethane.

In this specific case when $CO_2$ in step (c) it is charged with a loading rate or pressure gradient ranging from 3 to 20 bar/min, preferably 10 bar/min, until a pressure is reached in the pressure proof container ranging from 80 to 120 bar/min, more preferably 100 bar/min.

Precipitation of the polymer in this step is induced by the supercritical antisolvent which, by solubilizing and expanding the solution, causes a decrease in the solvent power of the liquid and simultaneous evaporation. The dissolved product, not soluble in the SCF, separates as a solid.

The particles in step (d) are washed with the antisolvent to remove the liquid completely before the precipitator is depressurized.

The depressurization in step (e) of the process according to the present invention is preferably carried out using a pressure gradient of 5 bar/min.

The preferred solvent used in step (a) to dissolve the biocompatible polysaccharide polymer is selected from dimethylsulfoxide and N-methylpyrrolidone.

The microspheres according to the present invention further comprising at least one of the above mentioned active principles can be prepared in two alternative ways.

The first one encompasses the addition of the active principle in step (a) of the process according to the present invention, after the dissolution of the biocompatible polysaccharide polymer in the aprotic solvent.

The coprecipitation of the active principle in step (c) with the biocompatible polysaccharide polymer does not alter the form or morphology of the precipitate.

According to the latter way, the microspheres coming from step (e), are suspended in a buffered solution preferably a phosphate buffer solution containing the desired active principle at a suitable concentration in order to obtain the desired active ingredient titer/mg of microsphere, and the suspension is subjected to liophylization at the liquid nitrogen temperature.

We report hereafter, for purely illustrative purposes, some examples of how to obtain microspheres made with polymer alone or with polymer containing pharmacologically active substances. Any variations which would be obvious to an expert in the field are to be considered as coming within the scope of the present invention.

EXAMPLE 1

Preparation of Microspheres Wherein the Starting Polymer is HYAFF-11 (Benzyl Ester of Hyaluronic Acid)

A hyaluronic acid ester, wherein all the carboxy groups of hyaluronic acid are esterified with benzyl alcohol, is dissolved in an aprotic solvent, such as dimethylsulfoxide (DMSO), at a concentration varying between 0.1 and 5% in weight, generally 1% w/w. Once the polymer has solubilized, the solution is poured into a pressure-proof container (precipitator), thermostatically controlled with a heated ethylene glycol jacket. Porous steel filters with an average cut-off of less than 0.1 $\mu$ are screwed onto the base and top of the precipitator.

The liquid is unable to seep through by gravity alone.

Once the container is closed, it is loaded from underneath with hyperpure carbon dioxide ($CO_2$) until the working pressure is reached (80–120 bar, preferably 100 bar). The $CO_2$ is dispersed in the solution through the filter. This antisolvent, which is first gaseous and then supercritical, can be mixed perfectly with the liquid solvent (DMSO) but it is a nonsolvent for the polymer.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the container and is released into the atmosphere. The solid particles, on the other hand, are trapped by the porous filters at the top and base of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution an antisolvent flow rate are set up.

At the end of washing, the supply of $CO_2$ is cut off and the container is depressurized at a race of 5 bar/min. The container is opened, the microspheres are collected and placed in suitable containers where they are stored at 4° C. The yield of microspheres is almost total. There is no appreciable incorporation of solvent in the precipitate.

The DMSO is collected in the expansion container.

The mean particle size in these working conditions is 0.6 $\mu$.

EXAMPLE 2

Preparation of Microspheres Wherein the Starting Polymer is HYAFF-11 p75 (Partial Benzyl Ester of Hyaluronic Acid)

A hyaluronic acid ester, wherein 75% of the carboxy groups of hyaluronic acid are esterified with benzyl alcohol, while the remaining part is salified with sodium, is dissolved in an aprotic solvent such as dimethylsulfoxide (DMSO), at a concentration varying between 0.1 and 5% in weigh, generally 1% w/w. Once the polymer has reached solubilization, the solution is poured into a pressure-proof container (precipitator) thermostatically controlled by a heated ethylene glycol jacket. Porous steel filters with a cut-off of 0.1 $\mu$ are screwed onto the top and base of the precipitator. The liquid is unable to seep through by gravity alone.

Once the vessel is close, it is loaded from underneath with hyperpure carbon dioxide ($CO_2$) until the working pressure is reached (80–120 bar, preferably 100 bar), he $CO_2$ is distributed in the solution through the porous filter. This antisolvent, which is first gaseous and then supercritical, can be mixed perfectly with the liquid solvent (DMSO) but it is a nonsolvent for the polymer.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a 10 millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is dispersed in the atmosphere. The solid particles, on the other hand, are trapped by the porous filters at the top and bottom of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

Figure 1:
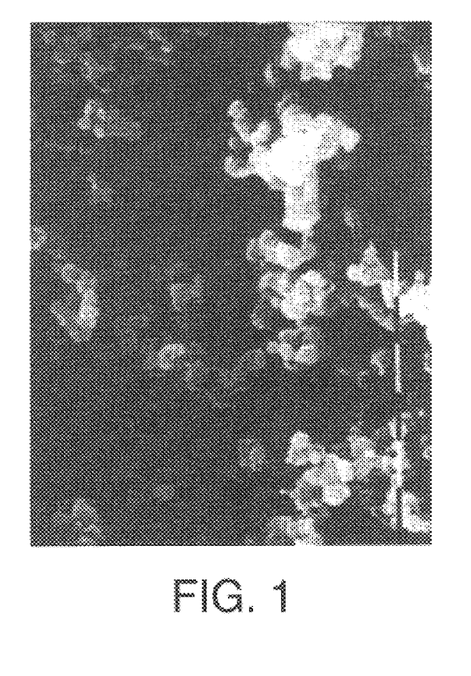
FIG. 1 represents a SEM photograph (Scanning Electron Microscope) of -HYAFF-11 microspheres obtained by following the operating conditions reported in Example 1, starting from a HYAFF concentration in DMSO equal to 1% w/w (bar=1 micron)
Figure 2:
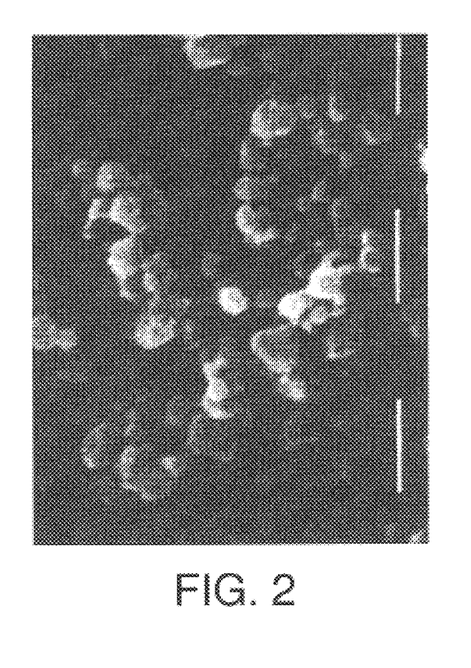
FIG. 2 is a photograph of the sample relative to FIG. 1 with a higher magnification (bar=1 micron)
Figure 3:
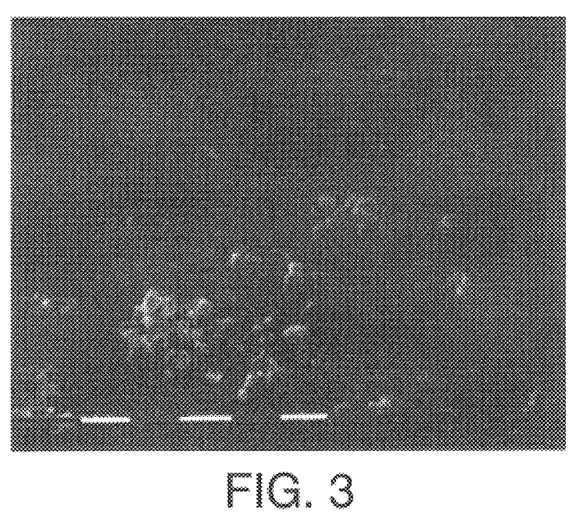
FIG. 3 represents a SEM photograph of HYAFF-11 microspheres obtained according to the working conditions of Example 2, starting from a HYAFF concentration in DMSO equal to 1% w/w (bar=1 micron)

The mean particle size in these working conditions is 0.8 $\mu$ (FIG. 3)

EXAMPLE 3

Preparation of Microspheres Wherein the Starting Polymer is HYAFF-7 (Ethyl Ester of Hyaluronic Acid)

A hyaluronic acid ester, wherein all the carboxy groups of hyaluronic acid are esterified with ethyl alcohol, is dissolved in an aprotic solvent such as dimethylsulfoxide (DMSO), at a concentration varying between 0.1 and 5% in weight, generally 1% w/w. Once the polymer has reached solubilization, the solution is poured into a pressure-proof vessel (precipitator), thermostatically controlled by a heated ethylene glycol jacket. Porous steel filters with a cut-off of 0.1 are screwed onto the top and bottom of the precipitator. The liquid is unable to seep through by gravity alone.

Once the vessel is closed, it is loaded from underneath with hyperpure carbon dioxide ($CO_2$) until the working pressure is reached (80–120 bar, preferably 100 bar). The $CO_2$) is distributed in the solution through the porous base. This antisolvent, which is first gaseous and then supercritical, can be mixed perfectly with the liquid solvent (DMSO) but it is a nonsolvent for the polymer.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and base of the precipitator. The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected acid placed in suitable containers where they are stored at 4° C. The field of microspheres is almost total. There is no appreciable incorporation of solvent in the precipitate. The DMSO is collected in the expansion container.

Figure 4:
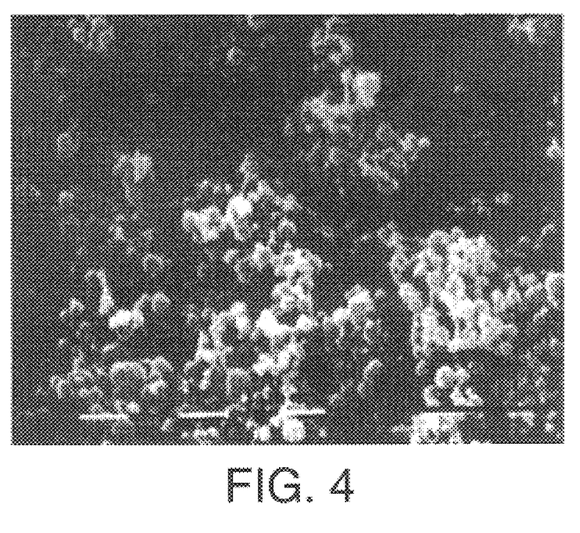
FIG. 4 represents a SEM photograph of HYAFF-7 microspheres prepared by following the operating conditions described in Example 3, starting from a HYAFF concentration in DMSO equal to 1% w/w (bar–1 micron)

The mean particle size in these working conditions is 1.0 $\mu$ (FIG. 4).

EXAMPLE 4

Preparation of Microspheres Wherein the Starting Polymer is a Crosslinked Polysaccharide of Hyaluronic Acid (ACP)

Figure 5:
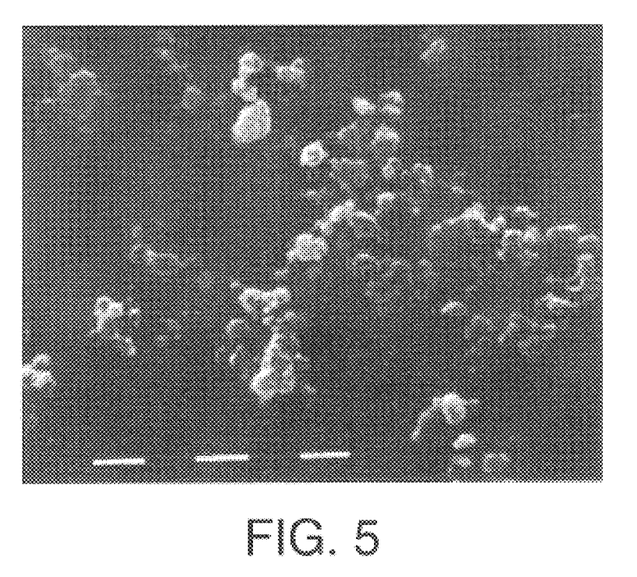
FIG. 5 represents a SEM photograph of ACP p10 microspheres obtained by following the operating conditions described in Example 4, starting from an ACP concentration in DMSO equal to 1% W/W (bar=1 micron)

A hyaluronic acid derivative, wherein 10% of the carboxy groups of hyaluronic acid are bound with inter- or intramolecular hydroxy groups and the remaining part is salified with sodium, is dissolved in an aprotic solvent such as dimethylsulfoxide (DMSO), at a concentration varying between 0.1 and 5% in weight, generally 1% w/w. The procedure described in Example 1 is then performed. The mean particle size is 0.6 $\mu$ (FIG. 5).

EXAMPLE 5

Preparation of Microspheres Wherein the Starting Polymer is an Ester of Alginic Acid (ALAFF)

Figure 6:
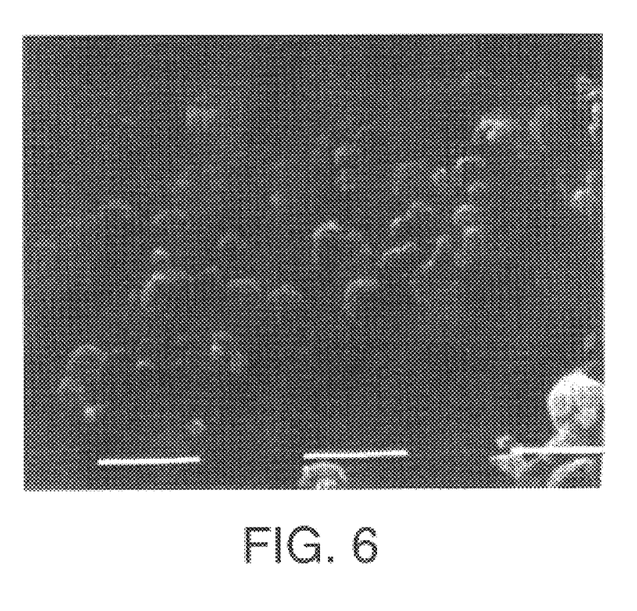
FIG. 6 represents a SEM photograph of ALAFF microspheres, prepared by following the operating conditions described in Example 5 starting from an ALAFF concentration in DMSO equal to 1% w/w (bar=1 micron).

A derivative of alginic acid, wherein all the carboxy groups of alginic acid are esterified with benzyl alcohol, is dissolved in an aprotic solvent, such as dimethylsulfoxide (DMSO), at a concentration varying between 0.1 and 5% in weight, generally 1% w/w. The procedure described in Example 1 is then performed. The mean particle size is 0.8 $\mu$ (FIG. 6).

EXAMPLE 6

Preparation of Microspheres Wherein the Starting Polymer is an ester of pectinic acid A derivative of pectinic acid, wherein all the carboxy groups are esterified with benzyl alcohol, is dissolved in an aprotic solvent, such as dimethylsulfoxide (DMSO), at a concentration varying between 0.1 and 5% in weight, generally 1% w/w. The procedure described in Example 1 is then performed.

The mean particle size is 0.7 $\mu$.

EXAMPLE 7

Preparation of Microspheres wherein the Starting Polymer is HYAFF-11 (Benzyl Ester of Hyaluronic Acid) and which are Loaded with Calcitonin A hyaluronic acid ester, wherein all the carboxy groups of hyaluronic acid are esterified with benzyl alcohol, is dissolved in an aprotic solvent such as dimethylsulfoxide (DMSO), at a concentration varying between 0.1% and 5% in weight, generally 1% w/w. Once the polymer has reached solubilization, the calcitonin is added to the polymeric solution at the set concentration, eg 1.5 I.U. per mg of polymer.

The solution thus obtained is poured into a pressure-proof vessel (precipitator), thermostatically controlled by a heated ethylene glycol jacket. Porous steel filters with a cut-off of 0.1 $\mu$ are screwed onto the top and base of the precipitator. The liquid is unable to seep through by gravity alone. Once the vessel is closed, it is loaded from underneath with hyperpure carbon dioxide ($CO_2$) until the working pressure is reached (80–120 bar, preferably 100 bar). The $CO_2$ is distributed in the solution through the porous base. This antisolvent, which is first gaseous and then supercritical, can be mixed perfectly with the liquid solvent (DMSO) but it is a nonsolvent for the polymer and the polypeptide calcitonin.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric Waive.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and base of the precipitator. The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

The mean particle size in these working conditions is 0.5 $\mu$. The quantity of incorporated calcitonin is 1.3 I.U. per mg of microspheres.

EXAMPLE 8

Preparation of Microspheres Wherein the Starting Polymer is HYAFF-11 p75 (Benzyl Ester of Hyaluronic Acid) and Which are Loaded with calcitonin A hyaluronic acid ester, wherein 75% of the carboxy groups of hyaluronic acid are esterified with benzyl alcohol, while the remaining part is salified with sodium, is dissolved in an aprotic solvent such as dimethylsulfoxide (DMSO), at a concentration varying between 0.1 and 5% in weight, generally 1m% w/w. Once the polymer has reached solubilization, calcitonin is added to the polymeric solution at a set concentration, eg 1.0 I.U. per mg of polymer.

The solution thus obtained is poured into a pressure-proof vessel (precipitator), thermostatically controlled by a heated ethylene glycol jacket. Porous steel filters with a cut-off of 0.1 $\mu$ are screwed onto the top and base of the precipitator. The liquid is unable to seep through by gravity alone.

Once the vessel is closed, it is loaded from underneath with hyperpure carbon dioxide ($CO_2$) until the working pressure is reached (80–120 bar, preferably 100 bar). The $CO_2$ is distributed in the solution through the porous filter. This antisolvent, which is first gaseous and then supercritical, can be mixed perfectly with the liquid solvent (DMSO) but it is a nonsolvent for the polymer and the polypeptide calcitonin.

The loading rate, or the pressure gradient over time, is set in a range of 3–20 bar/min, preferably 10 bar/min. The temperature in the precipitator is kept constant in a range of between 25° C. and 60° C. preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and base of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

The mean particle size in these working conditions is 0.8 $\mu$. The quantity of incorporated calcitonin is 0.9 I.U. per mg of microspheres.

EXAMPLE 9

Preparation of Microspheres wherein the Starting Polymer is HYAFF-7 (Ethyl Ester) of Hyaluronic Acid, and which are Loaded with Calcitonin A hyaluronic acid ester, wherein all the carboxy groups of hyaluronic acid are esterified with ethyl alcohol, is dissolved in an aprotic solvent such as dimethylsulfoxide (DMSO), at a concentration varying between 0.1 and 5% in weight, generally 1% w/w. Once the polymer has reached solubilization, calcitonin is added to the polymeric solution at a set concentration, eg 15 I.U. per mg of polymer.

The solution thus obtained is poured into a pressure-proof vessel (precipitator), thermostatically controlled by a heated ethylene glycol jacket. Porous steel filters with a cut-off of 0.1 $\mu$ are screwed onto the top and base of the precipitator. The liquid is unable to seep through by gravity alone.

Once the vessel is closed, it is loaded from underneath with hyperpure carbon dioxide ($CO_2$) until the working pressure is reached (80–120 bar, preferably 100 bar). The $CO_2$ is distributed in the solution through the porous base. This antisolvent, which is first gaseous and then supercritical, can be mixed perfectly with the liquid solvent (DMSO) but it is a nonsolvent for the polymer and the polypeptide calcitonin.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and bottom of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

The mean particle size in these working conditions is 1.0 $\mu$. The quantity of incorporated calcitonin is 13 I.U. per mg of microspheres.

EXAMPLE 10

Preparation of Microspheres Wherein the Starting Polymer is HYAFF-11 (Benzyl Ester of Hyaluronic Acid), and which Contain GMCSF (Granulocyte Macrophage Colony Stimulating Factor).

A hyaluronic acid ester, wherein all the carboxy groups of hyaluronic acid are esterified with benzyl alcohol, is dissolved in an aprotic solvent such as dimethylsulfoxide (DMSO), at a concentration which varies between 0.1 and 5% in weight, generally 1% w/w. Once the polymer has reached solubilization. GMCSF is added to the polymer solution at a set concentration. eg 1% of the polymer mass. The solution thus obtained is poured into a pressure-proof vessel (precipitator), thermostatically controlled by a heated ethylene glycol jacket. Porous steel filters with a cut-off of 0.1 $\mu$ are screwed onto the top and base of the precipitator. The liquid is unable to seep through by gravity alone.

Once the vessel is closed, it is loaded from underneath with hyperpure carbon dioxide ($CO_2$) until the working pressure is reached (80–120 bar, preferably 100 bar). The $CO_2$ is distributed in the solution through the porous base. This antisolvent, which is first gaseous and then supercritical, can be mixed perfectly with the liquid solvent (DMSO) but it is a nonsolvent for the polymer and the polypeptide GMCSF.

The loading rate, or the pressure gradient over time, is set in a range of 3 temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and bottom of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, he supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

The mean particle size in these working conditions is 1.0 $\mu$. The quantity of incorporated GMCSF is 0.9 $\mu$g per mg of microspheres.

EXAMPLE 13

Preparation of Microspheres Wherein the Starting Polymer is HYAFF-11 (Benzyl Ester of Hyaluronic Acid), and which are Loaded with Human Insulin A hyaluronic acid ester, wherein all the carboxy groups of hyaluronic acid are esterified with benzyl alcohol, is dissolved in an aprotic solvent such as dimethylsulfoxide (DMSO), at a concentration varying between 0.1 and 5% in weight, generally 1% w/w. Once the polymer has reached solubilization, human insulin is added to the polymeric solution at a set concentration, eg 5 I.U. per mg of polymer.

The solution thus obtained is poured into a pressure-proof vessel (precipitator), thermostatically controlled by a heated ethylene glycol jacket. Porous steel filters with a cut-off of 0.1$\mu$ are screwed onto the top and base of the precipitator. The liquid is unable to seep through by gravity alone.

Once the vessel is closed, it is loaded from underneath with hyperpure carbon dioxide ($CO_2$) until the working pressure is reached (80–120 bar, preferably 100 bar). The $CO_2$ is distributed in the solution through the porous base. This antisolvent, which is first gaseous and then supercritical, can be mixed perfectly with the liquid solvent (DMSO) but it is a nonsolvent for the polymer and the polypeptide human insulin.

The loading rate, or the pressure gradient over time, is set in a range of 3–20 bar/min, preferably 10 bar/min. The temperature in the precipitator is kept constant in a range of between 25° C. and 60° C., preferably 40° C.

When the working pressure has been reached, the flow of $CO_2$ is switched off for 10 minutes to obtain the desired pressure and temperature conditions inside the precipitator. The washing operation is begun by supply by supplying antisolvent to the precipitator and regulating the outlet flow from the top of the precipitator by means of a millimetric valve.

The outlet fluid, constituted by antisolvent and DMSO, is directed towards the DMSO collector, which is kept at room pressure; the DMSO separates after expansion and consequent cooling, while the gaseous $CO_2$ comes out of the top of the vessel and is released into the atmosphere. The solid particles, on the other hand, are trapped by the porous filters at the top and bottom of the precipitator.

The operation is continued to allow the DMSO to be completely removed from the precipitator. The time it takes for the organic solvent to be removed by the supercritical antisolvent depends on the temperature in the precipitation chamber, when fixed amount of liquid solution and antisolvent flow rate are set up.

At the end of washing, the supply of $CO_2$ is cut off and the vessel is depressurized at a rate of 5 bar/min. The vessel is opened, the microspheres are collected and placed in suitable containers where they are stored at 4° C. The yield of microspheres is almost total. There is no appreciable incorporation of solvent in the precipitate. The DMSO is collected in the expansion container.

The mean particle size in these working conditions is 0.8 $\mu$. The quantity of incorporated insulin is 5 I.U. per mg of microspheres.

EXAMPLE 14

Surface Loading of Microspheres of HYAFF-11 (Benzyl Ester of Hyaluronic Acid) with Calcitonin by Lyophilization Microspheres prepared according to Example 1 are suspended in a solution of 0.01 M phosphate buffer, containing calcitonin in a concentration which gives a protein titer of 1 I.U. per mg of suspended microspheres. After 15 minutes' shaking with a semiautomatic device, the container is immersed in liquid nitrogen until the suspension is completely frozen.

Once frozen, the container is lyophilized for 24 hours, after which the lyophilized product is stored at 4°C. The mean particle size in these working conditions is 0.4 $\mu$. The quantity of incorporated calcitonin is 1 I.U. per mg of microspheres.

EXAMPLE 15

Surface Loading of Microspheres of HYAFF-11 p75 (Benzyl Ester of Hyaluronic Acid) with Calcitonin by Lyophilization Microspheres prepared according to Example 2 are suspended in a solution of 0.01 M phosphate buffer, containing calcitonin in a concentration which gives a protein titer of 1.5 I.U. per mg of suspended microspheres. After 15 minutes' stirring with a semiautomatic device, the container is immersed in liquid nitrogen until the suspension is completely frozen.

Once frozen, the container is lyophilized for 24 hours, after which the lyophilized product is stored at 4° C.

The mean particle size in these working conditions is 0.6 $\mu$. The quantity of incorporated calcitonin is 1.5 I.U. per mg of microspheres.

What is claimed is:

1. A discontinuous process for the preparation of microspheres having a mean diameter of between 0.1 and 1$\mu$ and comprising a biocompatible polysaccharide, said process comprising the following steps:

a) dissolving the polysaccharide biocompatible polymer in an aprotic solvent at concentrations ranging from 0.1 to 5% by weight, b) charging the solution of step (a) in a pressure proof container having at the top and at the base steel filters with an average cut-off lower than 0.1 $\mu$;

c) loading the antisolvent from underneath until the pressure at which the fluid becomes supercritical at a temperature ranging from 25° to 60° C. is reached, d) removing the aprotic solvent with a flow of said supercritical fluid, e) depressurizing the pressure proof container, and collecting the precipitated product.

2. The process according to claim 1 wherein the fluid to be used under supercritical condition is selected from the group consisting of carbon dioxide, hydrofluorocarbons.

3. The process according to claim 2 wherein $CO_2$ is charged at a loading rate or pressure gradient ranging from 3 to 20 bar/min, until a pressure from 80 to 120 bar/min is reached in the pressure proof container.

4. The process according to claim 1 wherein said aprotic solvent used in step (a) to dissolve the biocompatible polysaccharide polymer is selected from dimethylsulfoxide and N-methylpyrrolidone.

5. The process according to claim 1 wherein said biocompatible polysaccharide polymer contained in the microspheres is an ester of an acidic polysaccharide selected from the group consisting of hyaluronic acid esters, crosslinked esters of hyaluronic acid, esters of chitin, esters of pectin, the esters of gellan, the esters of alginic acid.

6. The process according to claim 1 wherein said ester is the ethyl or benzyl ester of said acidic polisaccharide.

7. The process according to claim 1 for preparing microspheres comprising the partial ester or total benzyl ester of hyaluronic acid.

8. The process for preparing the microspheres according to claim 1 wherein the active principle is added in step (a), after the dissolution of the biocompatible polysaccharide polymer in the aprotic solvent.

9. The process for preparing the microspheres according to claim 1 wherein the microspheres from step (e), are suspended in a buffered solution containing the desired active principle at a suitable concentration in order to obtain the desired active ingredient titer/mg of microsphere, and the suspension is subjected to liophylization at the liquid nitrogen temperature.

10. An agro-alimentary product containing as a carrier the microspheres as claimed in claim 1.

11. A therapeutic method for the treatment of diseases associated with a gene defect comprising administering to a patient in need of such a treatment a therapeutically effective amount of said gene in a pharmaceutical compositions comprising said gene in a vehicle comprising microspheres having a mean diameter ranging from 0.1 to 1 $\mu$, said microspheres comprising an ester of biocompatible acidic polysaccharide polymer selected from the group consisting of: hyaluronic acid esters, crosslinked esters of hyaluronic acid, esters of chitin, esters of pectin, esters of gellan, esters of alginic acid.

12. The therapeutic method as claimed in claim 11 wherein said diseases are the consequence of a deficit or hyperactivity of an enzyme caused by defects in the gene encoding said enzyme.

13. The therapeutic method as claimed in claim 11 wherein said diseases are malformative diseases of genetic origin and hereditary diseases.

14. The therapeutic method as claimed in claim 11, wherein the microspheres comprise the partial or total benzyl ester of said acidic polysaccharide.

* * * * *